(12) United States Patent
Merz et al.

(10) Patent No.: US 8,742,470 B2
(45) Date of Patent: Jun. 3, 2014

(54) PH SENSOR AND MANUFACTURING METHOD

(75) Inventors: Matthias Merz, Leuven (BE); Coenraad Cornelis Tak, Waalre (NL); Romano Hoofman, Geel (BE)

(73) Assignee: NXP, B.V., Eindhoven (NL)

( * ) Notice: Subject to any disclaimer, the term of this patent is extended or adjusted under 35 U.S.C. 154(b) by 0 days.

(21) Appl. No.: 13/600,385

(22) Filed: Aug. 31, 2012

(65) Prior Publication Data

US 2013/0069120 A1 Mar. 21, 2013

(30) Foreign Application Priority Data

Sep. 16, 2011 (EP) ...................................... 11181700

(51) Int. Cl.
 *G01N 27/403* (2006.01)
(52) U.S. Cl.
 USPC ............................................................ 257/253
(58) Field of Classification Search
 USPC ............................................................ 257/253
 See application file for complete search history.

(56) References Cited

U.S. PATENT DOCUMENTS

| | | | | |
|---|---|---|---|---|
| 4,020,830 | A * | 5/1977 | Johnson et al. ............... | 600/348 |
| 4,940,945 | A | 7/1990 | Littlejohn et al. | |
| 5,342,498 | A | 8/1994 | Graves et al. | |
| 5,911,862 | A | 6/1999 | Chan | |
| 2007/0003209 | A1 | 1/2007 | Papautsky et al. | |
| 2008/0275327 | A1 * | 11/2008 | Faarbaek et al. ............... | 600/382 |
| 2011/0036913 | A1 * | 2/2011 | Merz et al. ..................... | 235/492 |

FOREIGN PATENT DOCUMENTS

| | | |
|---|---|---|
| CN | 2 410 639 Y | 12/2000 |
| CN | 101163440 A | 4/2008 |
| EP | 2 287 597 A1 | 2/2011 |

OTHER PUBLICATIONS

Anette Simonis et al., Miniaturised reference electrodes for field-effect sensors compatible to silicon chip technology Electrochimica Acta 51 (2005) 930-937.*

Simonis, A. et al. "Miniaturised Reference Electrodes for Field-Effect Sensors Compatible to Silicon Chip Technology," Electrochimica Acta 51, pp. 930-937 (2005).

Extended European Search Report for European Patent Appln. No. 11181700.3 (Mar. 13, 2012).

Office Action from counterpart application CN 2014033100972970 (Apr. 3, 2014).

* cited by examiner

*Primary Examiner* — Anthony Ho

(57) ABSTRACT

Disclosed is a pH sensor comprising a carrier (10) comprising a plurality of conductive tracks and an exposed conductive area (40) defining a reference electrode connected to one of said conductive tracks; a sensing device (30) mounted on the carrier and connected at least one other of said conductive tracks; an encapsulation (20) covering the carrier, said encapsulation comprising a first cavity (22) exposing a surface (32) of the sensing device and a second cavity (24) exposing the exposed conductive area, said second cavity comprising a reference electrode material (42) and an ion reservoir material (44) sharing at least one ion type with said reference electrode material, the reference electrode material being sandwiched between the exposed conductive area and the ion reservoir material. A method of manufacturing such a pH sensor is also disclosed.

20 Claims, 4 Drawing Sheets

PH SENSOR AND MANUFACTURING METHOD

CROSS-REFERENCE TO RELATED APPLICATIONS

Figure 1:
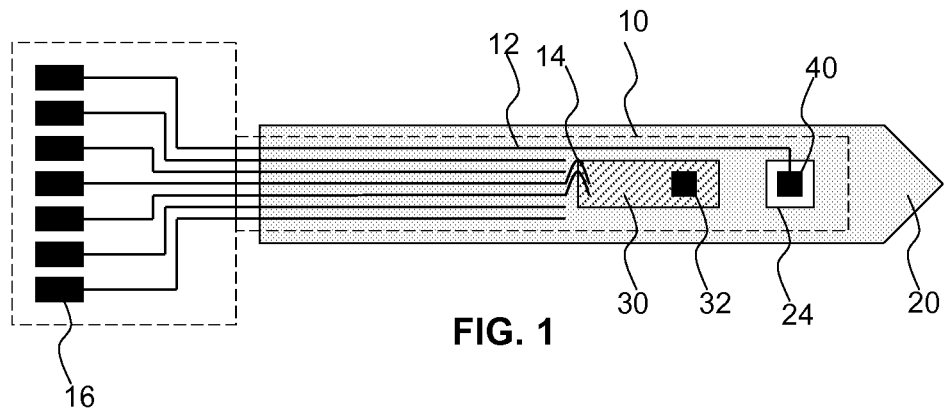

This application claims the priority under 35 U.S.C. §119 of European patent application no. 11181700.3, filed on Sep. 16, 2011, the contents of which are incorporated by reference herein.

FIELD OF THE INVENTION

The present invention relates to a pH sensor comprising a sensing device and a reference electrode. The present invention further relates to a method of manufacturing such a pH sensor.

BACKGROUND OF THE INVENTION

In many application domains, measurement of the pH of a solution or substance is important for a variety of reasons. In medical application domains, the measurement of the pH of a patient's blood can give valuable insights into the medical condition of the patient as pH values that deviate from expected values can indicate that the patient is suffering from some medical condition. pH sensors in this application domain are typically costly as they must comply with health and safety regulations in particular when the blood sample is returned to the patient, as well as be highly accurate In the food industry, the measurement of the pH of a food product, e.g. dairy products and meat, is often used as the pH is indicative of the condition of the food product. In such application domains, a high volume of measurements may have to be taken, either because of the large volumes of food or because the duration of the time period over which the food is stored. In such application domains, large numbers of (disposable) sensors may be required, which therefore requires the sensors to be cheap.

As is known per se, one of the main problems with the stability of pH sensors is that the reference electrode potential may not be stable over time, for instance because ion concentrations in a buffer solution to maintain the reference electrode potential leak away. Such buffer solutions may for instance be employed to protect the reference electrode from variations in the same ion concentration in the medium to be analyzed.

For instance, a commonly used reference electrode is a silver chloride electrode in which the reference potential E is defined by the Nernst equation:

$$E = E^0 - \frac{RT}{F} \ln a_{Cl^-}$$

In this equation, $E^0$ is the standard electrode potential, R is the ideal gas constant, T is the temperature, F is Faraday's constant and $a_{Cl^-}$ is the activity or effective concentration of the chloride ions. It will be immediately recognized that a change in the effective chloride concentration has a direct impact on the reference electrode potential E. Many silver chloride reference electrodes comprise a solution containing $Cl^-$ ions that needs periodic replenishing in order to maintain a stable reference potential.

This approach may not be suitable in application domains where the sensors are operated by staff that are not trained to replenish the reference electrode or perform recalibrations. Moreover, recalibration and refilling may be too expensive or cannot be performed at all for specific process applications, e.g. monitoring of food quality during transport.

Miniaturized pH sensors including reference electrodes are known per se. For instances, integrated circuits have been disclosed in which a plurality of sensors including a pH sensor and a reference sensor have been integrated on a single chip. However, the manufacturing process of such ICs is rather complex, such that the cost of such devices is prohibitive for low-end application domains such as the food industry.

SUMMARY OF THE INVENTION

The present invention seeks to provide a low-cost pH sensor having an integrated reference electrode with improved lifetime.

The present invention further seeks to provide a method of manufacturing such a pH sensor.

According to an aspect of the present invention, there is provided a pH sensor comprising a carrier comprising a plurality of conductive tracks and an exposed conductive area defining a reference electrode connected to one of said conductive tracks; a sensing device mounted on the carrier and connected at least one other of said conductive tracks; an encapsulation covering the carrier, said encapsulation comprising a first cavity exposing a surface of the sensing device and a second cavity exposing the exposed conductive area, said second cavity comprising a reference electrode material and an ion reservoir material sharing at least one ion type with said reference electrode material, the reference electrode material being sandwiched between the exposed conductive area and the ion reservoir material.

This pH sensor may be manufactured in a cost-effective manner as the footprint of the sensing device does not need to be increased because the reference electrode is incorporated in the package rather than the sensing device whilst the reference electrode at the same time provides a stable reference electrode potential due to the fact that the ion reservoir material, e.g. a gel containing a chloride salt solution such as a silver, potassium or sodium chloride solution, provides a chloride reservoir for the reference electrode material that defines the reference potential of the reference electrode, e.g. an Ag/AgCl paste, thereby ensuring that the chloride activity $a_{Cl^-}$ remains constant for the reference electrode formed by the reference electrode material and the exposed conductive area such as a bond pad, contact pad, landing or mounting pad and so on. Other suitable reference electrolytes may of course also be used.

Advantageously, the pH sensor further comprises a layer impermeable to the ion type in the ion reservoir material over the second cavity. This ensures that the chloride ion concentration in the reference electrode remains constant for prolonged periods of time, thus extending the lifetime of the pH sensor.

In an alternative embodiment, the encapsulation further comprises a fluid channel laterally extending from an edge of said encapsulation to the second cavity to keep the reference electrode in contact with the sample. The dimensions of the fluid channel, e.g. its diameter, are chosen such that the ions from the ion reservoir material, i.e. the reference electrolyte cannot (easily) escape the second cavity through the fluid channel, thus avoiding the large outdiffusion of chloride ions from the ion reservoir material. This may for instance be achieved by ensuring that the ion reservoir material has a large enough viscosity to prevent it from entering the fluid channel, and/or by dimensioning the fluid channel such that the contact area between the ion reservoir material and an external medium is reduced to such an extent that the outdiffusion of the relevant ions, e.g. chloride ions, is limited to insignificant amounts.

In yet another embodiment, the encapsulation further comprises a further fluid channel laterally extending from said edge to the first cavity. This establishes a liquid connection between the sensing device and the reference electrode, which prevents the pH sensor from floating due to the fact that a permanent liquid/fluid connection between the reference electrode and surface of sensing device or electrode is maintained, thus for instance preventing the occurrence of voltage spikes upon insertion of the pH sensor in a substance containing the analyte of interest.

In an embodiment, the pH sensor further comprising a first contact pad connected to the sensing device via one of said other of said conductive tracks and a second contact pad connected to the exposed conductive area via said one of said conductive tracks. This allows for an off-sensor processing of the sensing signals.

Alternatively, the sensing device comprises a transceiver, the pH sensor further comprising an antenna on the carrier connected to the at least one other of said conductive tracks. This allows for on-chip processing of the sensing signals, for instance if the exposed conductive area pad is connected to the sensing device via the second conductive track. The sensing device, e.g. an integrated circuit (IC) comprising a pH-sensitive surface such as an ion sensitive field effect transistor having its gate exposed in the first cavity, may be adapted to send the result of the sensing signal processing to a remote receiver, e.g. via a radio-frequency communication protocol.

In an embodiment, the carrier is a printed circuit board. This has the advantage that the first and second conductive tracks may be integral to the printed circuit board.

The pH sensor may further comprise a sharp tip to facilitate inserting the pH sensor into a substance such as a meat product. If such a sharp tip is combined with the presence of the first fluid channel, it is preferred that the first fluid channel is displaced with respect to the lateral axis through the sharp tip, such that the risk of blockage of the fluid channel by the substance upon its penetration is reduced.

In accordance with another aspect of the present invention, there is provided a method of manufacturing such a pH sensor, comprising providing a carrier having on its surface a plurality of conductive tracks, an exposed conductive area connected to one of said conductive tracks and a further exposed conductive area fixating an integrated circuit die to the further exposed conductive area, said integrated circuit die comprising an exposed pH-sensitive surface; encapsulating the resultant structure in a protective resin; forming first and second cavities in said protective resin, the first cavity exposing the pH-sensitive surface and the second cavity exposing the exposed conductive area; depositing a reference electrode material over the exposed conductive area; and depositing an ion reservoir material sharing at least one ion type with said reference electrode material over said reference electrode material.

This method has the advantage that a reference electrode can be provided in the packaging process of the pH sensor in a straightforward and therefore cost-effective manner.

Preferably, said encapsulating step and said cavities forming step are performed simultaneously. This provides an extremely cost-effective method of manufacturing the pH sensor of the present invention as the encapsulation process, e.g. an overmolding process such as the Boschman process in which the cavities are defined as exclusion areas, does not require additional processing steps to form the cavities in the encapsulation.

BRIEF DESCRIPTION OF THE EMBODIMENTS

Figure 2:
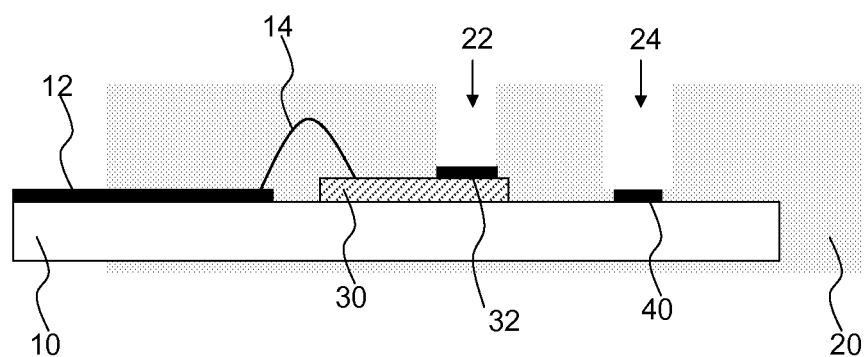
Figure 3:
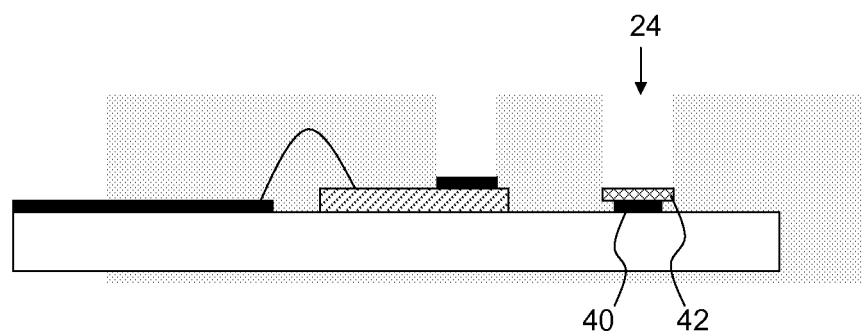
Figure 4:
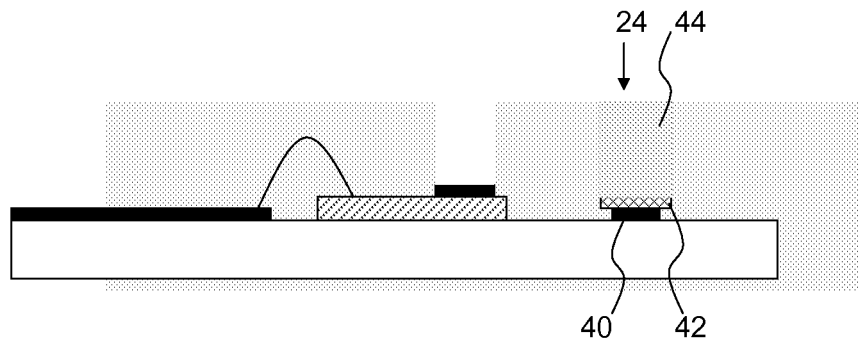
Figure 5:
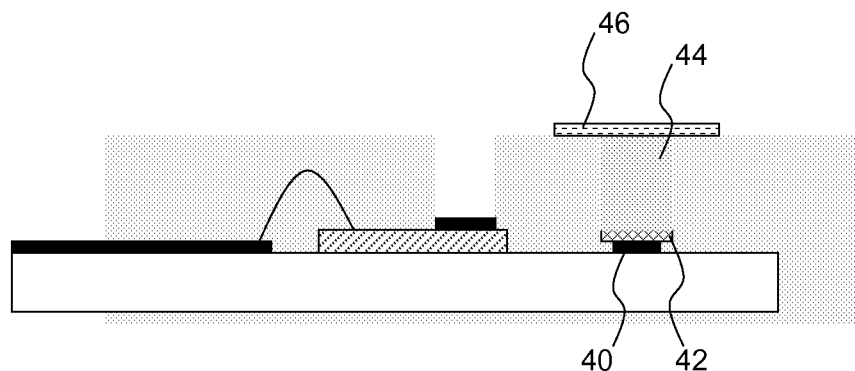
Figure 6:
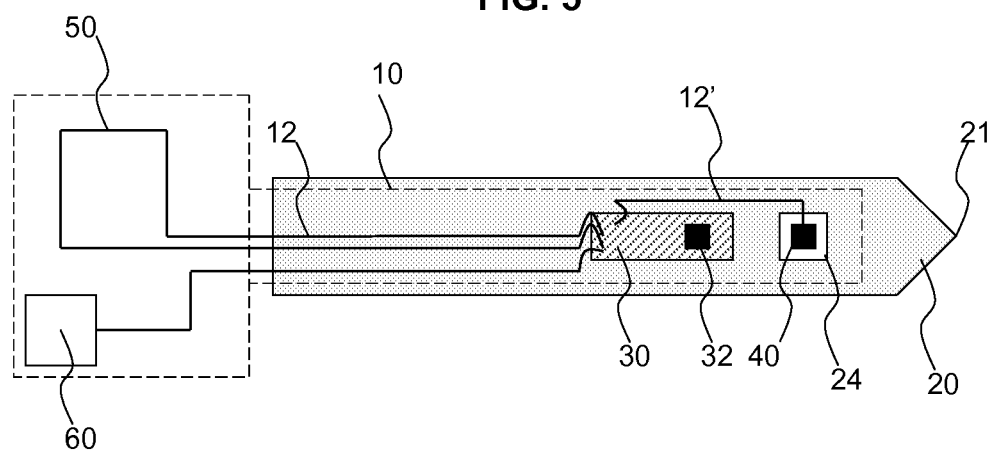
Figure 7:
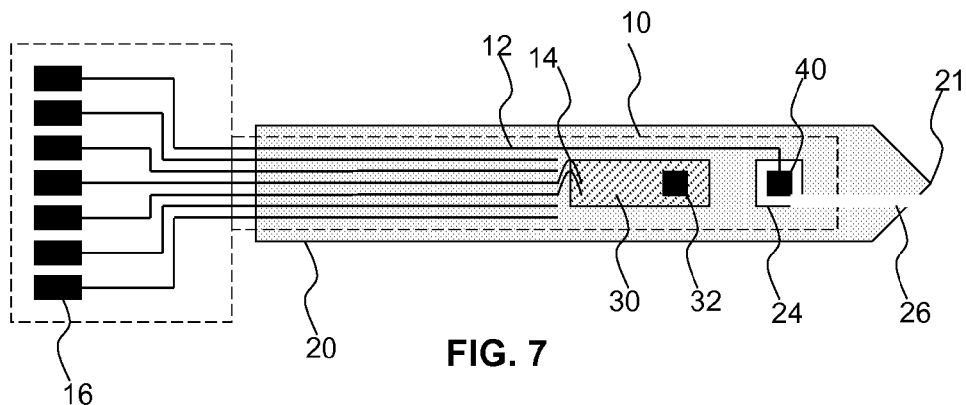
Figure 8:
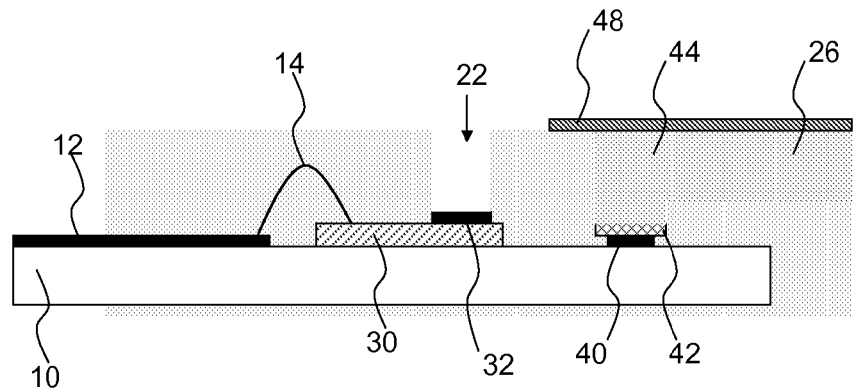
Figure 9:
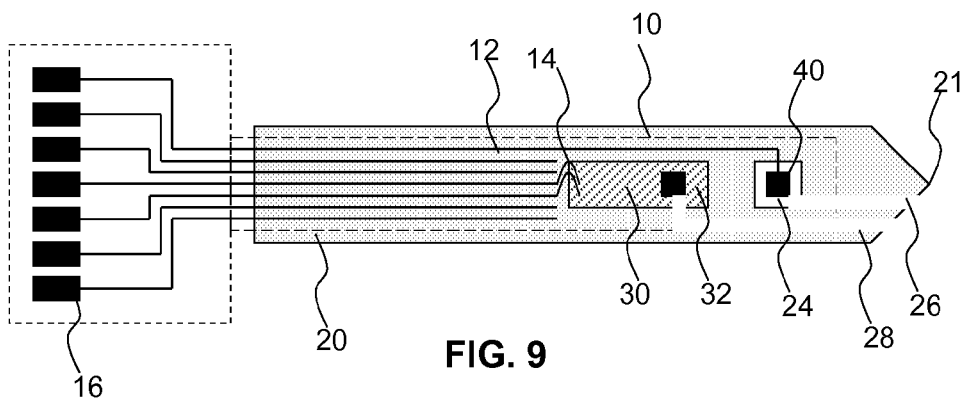
Figure 10:
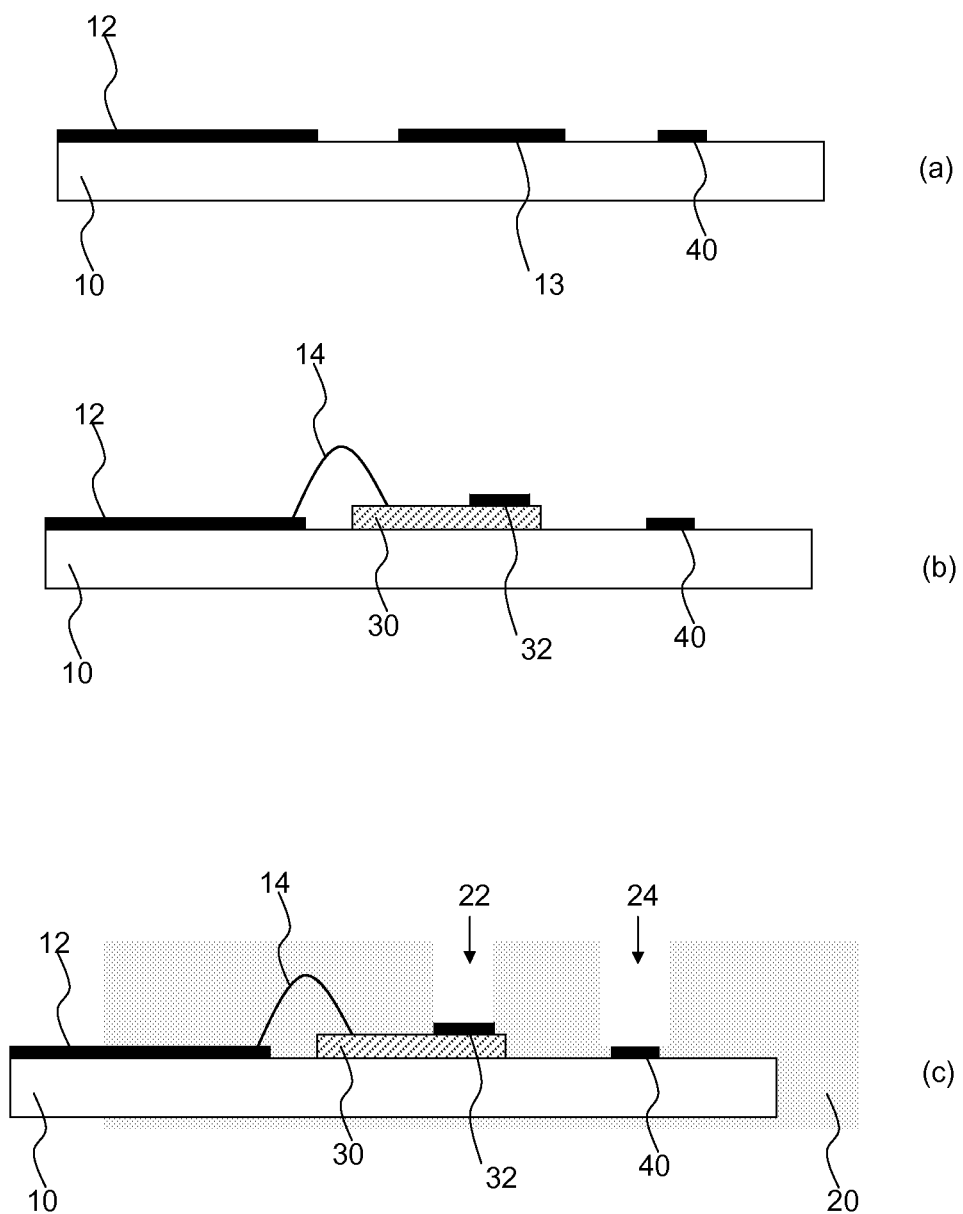

Embodiments of the invention are described in more detail and by way of non-limiting examples with reference to the accompanying drawings, wherein:

FIG. 1 schematically depicts a top view of an intermediate device according to an embodiment of the present invention;

FIG. 2 schematically depicts a cross section of the intermediate device of FIG. 1;

FIG. 3-5 schematically depict various steps of a method of completing the intermediate device of FIGS. 1 and 2;

FIG. 6 schematically depicts a top view of an intermediate device according to another embodiment of the present invention;

FIG. 7 schematically depicts a top view of a pH sensor according to yet another embodiment of the present invention;

FIG. 8 schematically depicts a cross section of the pH sensor of FIG. 7;

FIG. 9 schematically depicts a top view of a pH sensor according to a further embodiment of the present invention; and FIG. 10 schematically depicts various steps of a method of manufacturing an intermediate device such as shown in FIG. 2.

DETAILED DESCRIPTION OF THE DRAWINGS

It should be understood that the Figures are merely schematic and are not drawn to scale. It should also be understood that the same reference numerals are used throughout the Figures to indicate the same or similar parts.

FIG. 1 schematically depicts a top view, and FIG. 2 schematically depicts a cross-section of an intermediate structure of a pH sensor according to a first embodiment of the present invention. A carrier 10 such as a laminate or a printed circuit board (PCB) is equipped with a plurality of conductive tracks 12 such as a ribbon connector or metal tracks on the carrier, which connect to a plurality of contact pads 16. A sensing device 30 is attached to the carrier 10 in any suitable manner, for instance by adhesion to an exposed metal area such as a landing or mounting pad. The sensing device 30 has an exposed surface 32 that is pH-sensitive, that is, the surface 32 can be used to detect the pH of a substance brought into contact with the surface 32.

In an embodiment, the sensing device is a chip or integrated circuit (IC) die comprising an ion-sensitive field effect transistor (ISFET), which has a gate to which the surface 32 belongs. The gate may for instance be an extended gate, which may for instance be located on top of the metallization stack of the IC, and which may be made pH-sensitive by at least providing a coating of a pH-sensitive material such as $Ta_2O_5$ on the exposed surface 32 of the gate electrode. Extended gate ISFETs are well known per se. Since any suitable type of sensing device 30 may be used in the pH sensor of the present invention, the design of such sensing devices, and in particular of pH-sensitive ISFETs will not be described in further detail for the sake of brevity only.

The sensing device 30, e.g. IC die comprising at least one ISFET, may be connected to the conductive tracks 12 using any suitable connection means 14, e.g. bond wires or stud bumps. This facilitates access to the IC sensing die via the contact pads 16. The carrier 10 further comprises an exposed conductive area 40, e.g. a contact pad, bond pad, landing pad, mounting pad, an extended portion of a conductive track and so on, which may be made of any suitable material. As a non-limiting example, the exposed conductive area 40 may be a gold-plated copper contact pad. In the embodiment of the pH sensor shown in FIG. 1 and FIG. 2, the contact pad 40 is connected to one of the contact pads 16 via one of the conductive tracks 12.

The pH sensor is at least partially covered by an encapsulation 20, which protects the various components of the pH sensor from exposure to external elements, e.g. air, moisture, liquids and/or the analyte of interest. The encapsulation 20 may be formed in any suitable manner, e.g. over molding or injection molding, as will be explained in more detail later. The encapsulation 20 typically covers at least part of the carrier 10, the conductive tracks 12 and the sensing device 30. Any suitable molding material may be used, e.g. epoxy- or silicone-based compounds. The encapsulation 20 comprises a first cavity 22, which exposes the pH-sensitive surface 32 and a second cavity 24, which exposes the conductive area 40. The first cavity 22 and the second cavity 24 may have any suitable dimensions. The pH sensor may further comprise a sharp tip 21 to facilitate easy insertion of the pH sensor into a substance of interest, e.g. a meat sample.

The conductive area 40 exposed by the second cavity 24 forms part of the reference electrode of the pH sensor, which may be formed as shown in FIG. 3-5. As shown in FIG. 3, a reference electrode material, e.g. a paste 42 containing a suitable electrolyte for the reference electrode redox reaction, such as an Ag/AgCl containing paste, is deposited in the second cavity onto the conductive area 40 exposed by the second cavity 24, which forms the electrolyte source for the redox (half-)reaction at the reference electrode. Non-limiting examples of such a substance include E412 Ag/AgCl ink as provided by the Ercoinc Company, C61003P7 Ag/AgCl paste as provided by Gwent Electrical Materials Ltd. and 5876 screen-printable Ag/AgCl paste as provided by the DuPont Company.

In order to maintain constant levels of the relevant ions at the interface between the reference electrode and its environment e.g. (silver and) chloride ions, an ion reservoir material 44 containing at least the relevant type of ions also present in the reference electrode material 42, e.g. chloride ions in case of an Ag/AgCl containing paste 42, is deposited over the reference electrode material 42. Preferably, the ion reservoir material contains the relevant ion type in high concentrations, e.g. 1 to 4 M, for the material to act as a buffer for the reference electrode. The ion reservoir material 44 may be any suitable material, e.g. a gel such as agar-agar or cellulose, comprising a dissolved electrolyte, e.g. a chloride salt such as AgCl, KCl or NaCl. The ion reservoir material 44 is used to fill the remainder of the second cavity 24. This is shown in FIG. 4. To avoid the ions in the ion reservoir material 44, e.g. chloride ions, from escaping the second cavity 24, a film or membrane 46 is formed over the second cavity 24 as shown in FIG. 5, which may for instance be an ion-selective membrane such as a Nafion® membrane, that is largely or completely impermeable to the relevant ions, e.g., chloride ions. In this embodiment, the film or membrane 46 is permeable to the analyte of interest, i.e. H$^+$ ions, to allow electrical contact between the sample to be measured and the reference electrode as will be readily understood by the skilled person. As the film or membrane 46 prohibits the outdiffusion of chloride ions from the ion reservoir material, e.g. gel, 44 the potential of the reference electrode maintains constant over a prolonged period of time, thus extending the lifetime of the pH sensor. The film or membrane 46 may be kept in place using any suitable fixation technique, e.g. gluing, adhesion or lamination.

The above described pH sensor may be amended in a number of ways without departing from the scope of the present invention. One such a design variation is shown in FIG. 6, which depicts a top view of a sensing device 30 that comprises a RFID chip connected to an antenna 50, e.g. a loop antenna or any other suitable antenna design, and a power supply 60, e.g. a battery or an induction coil, via respective conductive tracks 12. The antenna 50 and power supply 60 may be placed inside or outside the molding 20.

In this embodiment, the RFID chip may be adapted to process the sensor readings on chip and send a pH reading to a remote receiver via the antenna 50, such that permanent contact with the pH sensor to obtain a sensor reading is unnecessary. In this embodiment, the conductive portion 40 exposed by the second cavity 24, such as a contact pad, of the reference electrode may be connected to the sensing device 30 via a further conductive track 12' to facilitate the on-chip processing of the sensor signals. The wireless connection allows for automated periodic monitoring of the pH of the substance under investigation, which may for instance be advantageous in application domains such as food quality monitoring, where such periodic readings can be used to monitor the deterioration of the food product beyond acceptable levels.

Access to the reference electrode of the pH sensor of the present invention is not limited to a semi-permeable membrane or film 46 sealing or covering the second cavity 24. An alternative embodiment is shown in FIG. 7 (top view) and FIG. 8 (cross-section). This embodiment of the pH sensor of the present invention comprises a fluid channel 26 that extends from an edge of the molding 20 to the second cavity 24, such that reference electrode material 42 and the ion reservoir material 44 in the reference electrode are in contact with the analyte of interest through the fluid channel 26. It is noted that the fluid channel 26 is dimensioned such that only a small section of the ion reservoir material 44 is in contact with the analyte of interest, thus preventing or at least reducing the outdiffusion of substantial amounts of chloride ions from the reference electrode.

In case of the presence of the sharp tip 21 at the insertion end of the pH sensor, it is preferred that the fluid channel 26 exits the molding 20 at the edge containing the sharp tip 21, and in such a manner that the fluid channel 26 is off-centered compared to the sharp tip 21, thus avoiding weakening of the sharp tip 21 that could lead to mechanical damage upon insertion of the pH sensor into a substance to be measured, as well as reducing the risk of the fluid channel 26 becoming block by the substance penetrating the fluid channel 26 upon insertion of the pH sensor in the substance.

In the embodiment shown in FIGS. 7 and 8, it is not necessary that the second cavity 24 is sealed by a (semi-)permeable layer or film 46 (although such a layer or film may still be used). Instead, the second cavity 24 may be sealed by an ion-impermeable film or sheet 48, which may be fixated into place in any suitable manner, e.g. gluing, adhering or laminating. Although the embodiment of FIGS. 7 and 8 is shown as a variation to the pH sensor depicted in FIG. 1-5, it is of course equally feasible to apply these variations to the design of the pH sensor shown in FIG. 6.

FIG. 9 shows a top view of yet another embodiment of a pH sensor of the present invention, which is a variation to the design shown in FIGS. 7 and 8. Compared to FIGS. 7 and 8, the pH sensor shown in FIG. 9 comprises a further fluid channel 28 that extends from an edge of the molding 20 to the first cavity 22, such that the pH sensing device and the reference electrode are kept in fluidic contact with each other via the fluid channels 26 and 28. This ensures that the sensing electrode 32 is kept biased rather than floating due to the fact that a permanent electrical connection between the sensing electrode of the sensing device 30 and the reference electrode is maintained through the sample, i.e. the substance to be measured. The top of the further fluid channel 28 may be sealed with a further film or sheet (not shown). Alternatively, the top of the further fluid channel 28 may be kept open as a single open side will only have a limited effect on the capillary force exerted within the further fluid channel 28 as long as this channel has been appropriately dimensioned.

A particular advantageous aspect of the present invention is that the reference electrode of the pH sensor is formed during the packaging process of the sensor. This has the advantage that the carrier such as a PCB only requires the presence of the conductive portion 40 connected to one of the conductive tracks 12, and that the sensing device 30 does not require complex manufacturing steps and additional area to facilitate the presence of a reference electrode on-chip.

It has been shown in FIG. 2-5 how a reference electrode may be formed in a pH sensor package comprising cavities 22 and 24 respectively exposing a sensing electrode of a sensing device 30 such as an IC die and a conductive area 40 forming the electrode surface of a reference electrode. FIG. 10 depicts a non-limiting example of how the package of FIG. 2 may be formed.

In step (a) a carrier 10 is provided such as a PCB, which comprises the exposed conductive area 40 in addition to conductive tracks 12 and a further conductive area 13 for receiving a die such as a mounting or landing pad 13. Such carriers are of course known per se and any suitable embodiment of such a carrier may be used.

Next, as shown in step (b), the sensing device 30 is fixated on the exposed conductive area 13, e.g. mounting pad, e.g. adhered, glued or otherwise fixated. Contacts (not shown) of the sensing device 30 are connected to the relevant conductive tracks 12 in any suitable manner, e.g. using bond wires 14. The sensing device 30 typically comprises an exposed sensing electrode 32 sensitive to $H^+$ concentrations, e.g. an extended gate of an ISFET. A suitable material for the gate electrode 32 is $Ta_2O_5$ although other pH-sensitive materials may also be used.

In the next step (c), the carrier 10 with mounted sensing device 30 is encapsulated in encapsulation 20. In a preferred embodiment, the cavities 22 and 24 that expose the sensing electrode 32 and the reference electrode surface 40 respectively are formed simultaneously with the encapsulation 20. This simultaneous step may further include the formation of the fluidic channels 26 and 28 if present. This simultaneous formation may for instance be achieved using a film-assisted molding process such as the so-called Boschman process or other suitable molding processes, e.g. overmolding. Preferably, the mold comprises exclusion areas defining the cavities 22 and 24.

In a film-assisted molding process, one or two plastic films are used to protect the mold. This film is sucked down into the inner surfaces of the mold, before the carrier 10 is loaded into the mold. This is followed by a transfer molding process, which is well-known per se.

The molding material is first liquified by heat and pressure, and then forced into closed mold cavities and held there under additional heat and pressure until all material is solidified (i.e. cured). After opening the mold, the encapsulated products are unloaded. Film-Assisted Molding offers a number of advantages over conventional transfer molding. These include the easy release of the encapsulated products from the mold, and the fact that surfaces such as the conductive area 40, pH sensitive surface 32 and contact pads 16 can be kept clear of the molding compound.

Although preferable, it is not essential to the present invention that the cavities 22 and 24 are formed during the encapsulation process. Alternatively, the cavities 22 and 24 may be formed after the encapsulation 20 is formed, e.g. by means of laser cutting.

Other alternative manufacturing methods may be contemplated. For instance, the carrier 10 may be provided in a pre-molded package 20 in which the sensing device 30 is subsequently placed, and which may be sealed with e.g. an epoxy resin after the formation of the contacts, e.g. bond wires 14, between the sensing device 30 and the conductive tracks 12.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A pH sensor comprising:
a carrier comprising a plurality of conductive tracks and an exposed conductive area defining a reference electrode connected to a first track of said plurality of conductive tracks;
a sensing device mounted on the carrier and connected to at least a second track of said plurality of conductive tracks;
an encapsulation covering the carrier, said encapsulation comprising:
a first cavity exposing a surface of the sensing device, and
a second cavity exposing the exposed conductive area, said second cavity comprising a reference electrode material and an ion reservoir material sharing at least one ion type with said reference electrode material, the reference electrode material being sandwiched between the exposed conductive area and the ion reservoir material.

2. The pH sensor of claim 1, further comprising:
a layer impermeable to the at least one ion type in the ion reservoir material over the second cavity.

3. The pH sensor of claim 1, further comprising:
a first contact pad connected to the sensing device via the second track; and
a second contact pad connected to the exposed conductive area via the first track.

4. The pH sensor of claim 1, wherein the sensing device comprises a transceiver, the pH sensor further comprising:
an antenna on the carrier connected to the second track.

5. The pH sensor of claim 4, wherein the exposed conductive area is connected to the sensing device via the first track.

6. The pH sensor of claim 1, wherein said encapsulation further comprises:

a first fluid channel laterally extending from an edge of said encapsulation to the second cavity.

7. The pH sensor of claim 6, wherein said encapsulation further comprises:
a second fluid channel laterally extending from said edge to the first cavity.

8. The pH sensor of claim 7, wherein the first fluid channel and the second fluid channel maintain a permanent electrical connection between the sensing device and the reference electrode.

9. The pH sensor of claim 7, wherein the first fluid channel and the second fluid channel are formed simultaneously.

10. The pH sensor of claim 1, wherein the carrier is a printed circuit board.

11. The pH sensor of claim 1, wherein the sensing device comprises an ion sensitive field effect transistor (ISFET) having its gate exposed in the first cavity.

12. The pH sensor of claim 11, wherein the gate of the ISFET comprises $Ta_2O_5$.

13. The pH sensor of claim 1, further comprising:
a sharp tip configured to insert the pH sensor into a substance.

14. The pH sensor of claim 13, wherein a fluid channel is off-centered compared to the sharp tip.

15. The pH sensor of claim 1, wherein the exposed conductive area comprises a gold-plated copper layer.

16. The pH sensor of claim 1, wherein the reference electrode material comprises Ag and AgCl and the ion reservoir material comprises chloride ions.

17. The pH sensor of claim 16, further comprising:
an ion-selective membrane impermeable to the at least one ion type in the ion reservoir material over the second cavity.

18. The pH sensor of claim 1, wherein the reference electrode is formed during a packaging process.

19. A method of manufacturing a pH sensor comprising:
providing a carrier having on its surface a plurality of conductive tracks, a first exposed conductive area connected to one of said conductive tracks and a second exposed conductive area;
fixating an integrated circuit die to the second exposed conductive area, said integrated circuit die comprising an exposed pH-sensitive surface;
encapsulating the resultant structure in a protective resin;
forming first and second cavities in said protective resin, the first cavity exposing the pH-sensitive surface and the second cavity exposing the first exposed conductive area;
depositing a reference electrode material over the first exposed conductive area; and
depositing an ion reservoir material sharing at least one ion type with said reference electrode material over said reference electrode material.

20. The method of claim 19, wherein said encapsulating step and said forming step are performed simultaneously.

* * * * *